United States Patent
Khoury et al.

(10) Patent No.: US 10,238,614 B2
(45) Date of Patent: Mar. 26, 2019

(54) USES OF 6-AMINOHEXANOIC ACID TO MANAGE BLEEDING CONDITIONS

(71) Applicant: EMORY UNIVERSITY, Atlanta, GA (US)

(72) Inventors: Hanna Jean Khoury, Atlanta, GA (US); Ana Antun, Atlanta, GA (US)

(73) Assignee: Emory University, Atlanta, GA (US)

( * ) Notice: Subject to any disclaimer, the term of this patent is extended or adjusted under 35 U.S.C. 154(b) by 154 days.

(21) Appl. No.: 14/779,246

(22) PCT Filed: Mar. 26, 2014

(86) PCT No.: PCT/US2014/031803
§ 371 (c)(1),
(2) Date: Sep. 22, 2015

(87) PCT Pub. No.: WO2014/160742
PCT Pub. Date: Oct. 2, 2014

(65) Prior Publication Data
US 2016/0067200 A1   Mar. 10, 2016

Related U.S. Application Data

(60) Provisional application No. 61/805,542, filed on Mar. 27, 2013.

(51) Int. Cl.
*A61K 31/197* (2006.01)

(52) U.S. Cl.
CPC .................. *A61K 31/197* (2013.01)

(58) Field of Classification Search
CPC .................................................... A61K 31/197
See application file for complete search history.

(56) References Cited

U.S. PATENT DOCUMENTS

| | | | |
|---|---|---|---|
| 3,457,347 A | 7/1969 | Rubricius | |
| 5,415,863 A | 5/1995 | Williams | |
| 7,078,479 B2 | 7/2006 | Rojkaer | |
| 2004/0006020 A1* | 1/2004 | Rojkjaer | A61K 31/198 424/94.64 |
| 2008/0275016 A1 | 11/2008 | Arbiser | |
| 2009/0191180 A1* | 7/2009 | Viuff | A61K 38/4846 424/94.64 |

OTHER PUBLICATIONS

Amicar(R) (aminocaproic acid) product label NDA 15-230/S-037, Sep. 2008.
Antun et al., 2013, Epsilon aminocaproic acid prevents bleeding in severely thrombocytopenic patients with hematological malignancies 119(21) 3784-3787.
Deysine et al. Mechanism of Action of Epsilon Aminocaproic Acid in the Control of Hemorrhage, Annals of the New York Academy of Sciences, 1964, vol. 115, issue 2, pp. 291-297.
FDA approved Label Aminocaproic acid syrup USP 25% for Application No. 74759, May 1998.
Florentino-Pineda et al, 2001, The Effect of ε-Aminocaproic Acid on Perioperative Blood Loss in Patients With Idiopathic Scoliosis Undergoing Posterior Spinal Fusion: A Preliminary Prospective Study, Spine 26(10), 1147-1151.
Garwal et al. Anti-fibrinolytic therapy with aminocaproic acid for the control of bleeding in thrombocytopenic patients, Scand J Haematol. 1985, 35(5):497-500.
Kalmadi et al. Epsilon aminocaproic acid reduces transfusion requirements in patients with thrombocytopenic hemorrhage, Cancer. 2006, 107(1):136-40.
Mannuccio, Hemostatic Drugs, N Engl J Med, 1998; 339: 245-253.
Schwartz et al. Epsilon-aminocaproic acid in the treatment of patients with acute promyelocytic leukemia and acquired alpha-2-plasmin inhibitor deficiency, Ann Intern Med. 1986, 105(6):873-7.
Thorsen et al. 1974, Rate of Activation and Electrophoretic Mobility of Unmodified and Partially Degraded Plasminogen Effects of 6-Aminohexanoic Acid and Related Compounds, Scandinavian Journal of Clinical and Laboratory Inverstigation 34(2), 1670176.
Wassenaar et al. Acute promyelocytic leukaemia and acquired alpha-2-plasmin inhibitor deficiency: a retrospective look at the use of epsilon-aminocaproic acid (Amicar) in 30 patients, Hematol Oncol. 2008, 26(4): 241-6.

* cited by examiner

*Primary Examiner* — Craig D Ricci
*Assistant Examiner* — Christopher R Stone
(74) *Attorney, Agent, or Firm* — Emory Patent Group

(57) ABSTRACT

This disclosure relates to the use of EACA (6-aminohexanoic acid) as an antifibrinolytic for the prevention of thrombocytopenic bleeds. In certain embodiment, the disclosure relates to methods of preventing bleeding in patients with thrombocytopenia resulting from hematological malignancies by administering 6-aminohexanoic acid, salts, or prodrugs thereof prophylactically to a subject in need thereof. In certain embodiments, subjects with stable chronic thrombocytopenia previously managed with platelet transfusion represent a selected group of patients that benefit from prophylaxis.

11 Claims, 1 Drawing Sheet

| | |
|---|---|
| Age, years median (range) | 61 (17-82) |
| Male/female | 29/15 |
| Platelet counts x10⁹/L when EACA started, median (range) | 8 (1 – 19) |
| Patients with platelet refractoriness n (%) | 10 (23%) |
| Duration of thrombocytopenia in days, median (range) | 273 (20-1463) |
| Diagnosis n (%)<br>AML<br>AML<br>ALL<br>MDS<br>CLL<br>ITP<br>Lymphoma<br>Aplastic anemia<br>Myelofibrosis | <br>9 (21)<br>14 (32)<br>1 (2)<br>15 (35)<br>1 (2)<br>1 (2)<br>1 (2)<br>1 (2)<br>1 (2) |
| Disease Status of patients at the time EACA started<br>  Active treatment, n (%)<br>  Relapsed/refractory, n (%) | <br>13 (29)<br>31 (71) |
| Duration of EACA therapy, median(range) in days | 47 (7-209) |
| Patients without bleeding on EACA, n (%) | 26 (59) |
| Patients with bleeding episodes while on EACA, n (%)<br>Patients requiring platelet transfusions for bleeds, n (%) | 18 (41)<br>7 (16%) |
| Grade and location of the 10 bleeding episodes requiring platelet transfusions:<br>  Grade 4 – CNS*<br>  Grade 3 – rectal<br>  Grade 2 – hemorrhoids<br>  Grade 2 – hematuria **<br>  Grade 2 – epistaxis<br>  Grade 2 – oral<br>  Grade 2 – vaginal | <br>1<br>1<br>1<br>2<br>1<br>3<br>1 |
| Grade and location of the 19 bleeding episodes not requiring platelet transfusions:<br>Grade 1- epistaxis<br>Grade 1 – skin bruises<br>Grade 1 – gingival bleed<br>Grade 1 - vaginal<br>  Grade 2 – gingival<br>  Grade 2 – vaginal<br>  Grade 2 - epistaxis | <br>7<br>4<br>2<br>1<br>2<br>1<br>2 |
| Reason for discontinuing EACA, n (%)<br>  Death<br>  Increased platelets count<br>  Hematuria | <br>25 (57)<br>18 (41)<br>1 (2) |

USES OF 6-AMINOHEXANOIC ACID TO MANAGE BLEEDING CONDITIONS

CROSS REFERENCE OF RELATED APPLICATIONS

This Application claims priority to U.S. Provisional Application No. 61/805,542 filed the 27 Mar. 2013, hereby incorporated by reference in its entirety.

BACKGROUND

Thrombocytopenia is frequently chronic, severe, and occasionally refractory to platelet transfusions in patients with marrow failure syndromes and hematological malignancies. Despite prophylactic allogeneic platelet transfusions, maintaining platelet counts in a safe range is often difficult in this patient population. Bleeding complications occur in approximately 20% of patients with acute myeloid leukemia and in up to 58% of hematopoietic stem cell transplants recipients. Thus, there is a need to identify improved therapeutic methods to control thrombocytopenia.

AMICAR® is an FDA approved product containing epsilon aminocaproic acid (EACA) (6-aminohexanoic acid) reported to enhance hemostasis when fibrinolysis contributes to bleeding. For the treatment of acute bleeding syndromes due to elevated fibrinolytic activity, the label of AMICAR® indicates using 5 AMICAR® 1000 mg tablets or 10 AMICAR® 500 mg tablets (5 g) or 20 milliliter of AMICAR® oral solution (5 g) that is to be administered during the first hour of treatment.

Kalmadi et al. report that EACA reduces transfusion requirements in patients with thrombocytopenic hemorrhage. Cancer, 2006, 107, 136-140. Schwartz et al., report EACA in the treatment of patients with acute promyelocytic leukemia and acquired alpha-2-plasmin inhibitor deficiency. Ann Intern Med, 1986, 105(6):873-7. See also Wassenaar et al., Hematol Oncol, 2008, 26(4):241-6; Garewal and Durie, Scand J Haematol, 1985, 35, 497-500; Deysine and Cliffton, Annals of the New York Academy of Sciences, 1964, 115, 291-297; Mannucci, New England Journal of Medicine, 1998, 339, 245-253; and U.S. Pat. No. 5,415,863.

Antun et al. report epsilon aminocaproic acid prevents bleeding in severely thrombocytopenic patients with hematological malignancies. Cancer. 2013, 1;119(21):3784-7.

References cited herein are not an admission of prior art.

SUMMARY

This disclosure relates to the use of EACA (6-aminohexanoic acid) as an antifibrinolytic for the prevention of thrombocytopenic bleeds. In certain embodiment, the disclosure relates to methods of treating or preventing bleeding in patients with thrombocytopenia resulting from hematological malignancies by administering 6-aminohexanoic acid, salts, or prodrugs thereof prophylactically to a subject in need thereof. In certain embodiments, subjects with stable chronic thrombocytopenia previously managed with platelet transfusion represent a selected group of patients that benefit from prophylaxis.

In certain embodiments, the disclosure contemplates methods of treating or preventing excessive bleeding comprising administering e.g., once, twice, or three times daily, a pharmaceutical composition comprising 6-aminohexanoic acid, salt, or prodrug thereof to a subject in need thereof, e.g., human subject, diagnosed with cancer or a hematological disorder.

In certain embodiments, the subject is on a chemotherapy or immunotherapy.

In certain embodiments, the disclosure contemplates methods of treating or preventing excessive bleeding comprising administering e.g., once or twice daily, a pharmaceutical composition comprising about 0.1 to 4.0 grams of 6-aminohexanoic acid or molar equivalent salt thereof to a subject in need thereof, e.g., human subject, diagnosed with a hematological disorder.

In certain embodiments, the subject receives about 2.0 grams of 6-aminohexanoic acid or molar equivalent salt thereof daily, e.g., wherein administration is twice daily a pharmaceutical composition comprising about 1.0 gram of 6-aminohexanoic acid or molar equivalent salt thereof.

In certain embodiments, the administration is sustained as long as or until a measured platelet count is greater than $20 \times 10^9$/L, $25 \times 10^9$/L, $30 \times 10^9$/L, $35 \times 10^9$/L, or $40 \times 10^9$/L.

In certain embodiments, the administration is sustained for greater than 20, 30, or 40 days.

In certain embodiments, the hematological disorder is chronic immune thrombocytopenia, aplastic anemia, or a hematological malignancy such as leukemia, acute lymphoblastic leukemia (ALL), acute myelogenous leukemia (AML), chronic lymphocytic leukemia (CLL), small lymphocytic lymphoma (SLL), chronic myelogenous leukemia (CML), acute monocytic leukemia (AMoL), lymphoma, Hodgkin's lymphoma, or Non-Hodgkin's lymphoma.

In certain embodiments, the subject received an autologous or allogeneic hematopoietic stem cell transplantation, bone marrow transplant, or peripheral stem cell transplantation.

In certain embodiments, the administration is in combination with a platelet transfusion or not done in combination with a platelet transfusion.

In certain embodiments, the subject is less than 18, 12, or 6 years of age.

In certain embodiments, the administration is oral solution or tablet.

BRIEF DESCRIPTION OF THE FIGURES

FIG. 1 shows a table of the characteristics of 44 thrombocytopenic patients who received epsilon aminocaproic acid for the prevention of bleeding. CML is chronic myeloid leukemia, AML is acute myeloid leukemia, ALL is acute lymphoblastic leukemia, MDS is myelodysplastic syndrome, CLL is chronic lymphocytic leukemia, ITP is immune thrombocytopenic purpura. *Traumatic brain injury in a car accident **One patient had 2 episodes of hematuria.

DETAILED DISCUSSION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. An ester of a carboxylic acid group is contemplated prodrug. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g., patient) is cured and the condition or disease is eradicated. Rather, embodiments, of the present disclosure also contemplate treatment that merely reduces symptoms, and/or delays conditions or disease progression.

As used herein, the term "combination with" when used to describe administration with an additional treatment means that the agent may be administered prior to, together with, or after the additional treatment, or a combination thereof.

EACA Prevents Bleeding in Severely Thrombocytopenic Patients with Hematological Malignancies Individuals with hematological malignancies (leukemia) and bone marrow failure often have low platelet count as a result of the effects of their underlying disease or the effects of chemotherapy on the blood forming cells in bone marrow, i.e., thrombocytopenia. A common diagnostic criteria used for thrombocytopenia is a low platelet count compared to the normal range of platelets. As the platelet count falls associated bleeding complications tend to increase. These include bleeding in the mouth and gum, bruising, nosebleeds, rash (pinpoint red spots called petechiae) and excessive, uncontrolled bleeding from cuts or wounds. Thrombocytopenia-associated bleeding remains a significant problem (up to 50% of diagnosed patients have bleeding complications). The standard of care is prophylactic platelet transfusion.

In the absence of an intervention that increases platelet production or accelerates platelet recovery, recurrent platelet transfusions remain the option for patients with severe chronic thrombocytopenia associated with hematological malignancies. This approach necessitates frequent visits to the medical center, is hampered by platelet shortages, and ultimately often leads to alloimmunization and platelet refractoriness. Additionally, this approach is ineffective in preventing significant bleedings in 20-50% of patients.

In one study disclosed herein, EACA was administered in patients with transfusion-dependent thrombocytopenia. Patients were managed in the outpatient setting despite their severe thrombocytopenia and received EACA as a substitution for prophylactic, threshold directed platelet transfusion. Patients reported rapid disappearance of petechiae and resolution of subcutaneous bleeds shortly after initiation of EACA. With a median duration of EACA administration of 47 days, but ranging up to 209 days, no major spontaneous bleeds were observed in these patients, whose median platelet counts were $8 \times 10^9$/L and for whom no prophylactic platelet transfusions were administered. Two grade 3-4 bleedings occurred in the setting of a trauma and from a pre-existing condition. Only 16% of the patients received platelet transfusions (median of 4 units).

EACA is safe and is associated with a low risk of major spontaneous bleeding in severe and refractory thrombocytopenic patients with hematological disorders not receiving prophylactic platelet transfusion.

Administration

In certain embodiments, the disclosure contemplates methods of treating or preventing excessive bleeding comprising administering e.g., once, twice, or three times daily doses, a pharmaceutical composition comprising 6-aminohexanoic acid, salt, or prodrug thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.1 to 4.0 grams of 6-aminohexanoic acid or molar equivalent salt thereof to a subject in need thereof, e.g., human subject, diagnosed with a hematological disorder.

In certain embodiments, the subject receives about 2.0 grams of 6-aminohexanoic acid or molar equivalent salt thereof daily, e.g., wherein administration is twice daily a pharmaceutical composition comprising about 1.0 grams of 6-aminohexanoic acid or molar equivalent salt thereof.

In certain embodiments, the disclosure contemplates methods of treating or preventing excessive bleeding comprising administering e.g., once or twice daily, a pharmaceutical composition comprising about 0.5 to 4.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.5 to 3.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.5 to 2.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.75 to 1.5 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering twice daily a pharmaceutical composition comprising about 0.5 to 1.5 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.75 to 1.25 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.75 to 4.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.75 to 3.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 0.75 to 2.0 grams of 6-aminohexanoic acid or molar equivalent salt thereof to a subject in need thereof, e.g., human subject, diagnosed with a hematological disorder.

In certain embodiments, the subject receives about 1.5 to 2.5 grams of 6-aminohexanoic acid or molar equivalent salt thereof daily. In certain embodiments, the subject receives about 1.5 to 3.5 grams of 6-aminohexanoic acid or molar equivalent salt thereof daily.

In certain embodiments, the subject receives about 1.5 to 4.5 grams of 6-aminohexanoic acid or molar equivalent salt thereof daily.

In certain embodiments, the disclosure contemplates methods of treating or preventing excessive bleeding comprising administering e.g., once or twice daily, a pharmaceutical composition comprising about 4.0 to 5.0 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 5.0 to 50 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 5.0 to 30 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 5.0 to 25 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about 5.0 to 10 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about less than 1, 2, 5, 15, 20, 25, 30, or 50 grams of 6-aminohexanoic acid or molar equivalent salt thereof to a subject in need thereof, e.g., human subject, diagnosed with a hematological disorder.

In certain embodiments, the disclosure contemplates methods of treating or preventing excessive bleeding comprising administering e.g., once or twice daily, a pharmaceutical composition comprising about more than 1, 2, 5, 15, 20, 25, 30, or 50 grams of 6-aminohexanoic acid or molar equivalent salt thereof to a subject in need thereof, e.g., human subject, diagnosed with a hematological disorder.

In certain embodiments, the administration is sustained according to doses provided herein until a measured platelet count is greater than $20\times10^9$/L, $25\times10^9$/L, $30\times10^9$/L, $35\times10^9$/L, or $40\times10^9$/L.

In certain embodiments, the administration is sustained for greater than 20, 30, or 40 days.

Combination Therapies

In certain embodiments, the administration of 6-amionhexanoic acid is in combination with a platelet transfusion or not done in combination with a platelet transfusion.

In certain embodiments, the administration is in combination with a chemotherapy or immunotherapy.

Chemotherapy may entail administration of 6-amionhexanoic acid in combination with gefitinib, erlotinib, docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

Immunotherapy may entail administration of 6-amionhexanoic acid in combination with cyclophosphamide, abatacept, abetimus, adalimumab, afelimomab, alefacept, anakinra, anti-IL-6, anti-thymocyte globulin, ascomycin, azathioprine, basiliximab, belimumab, briakinumab, certolizumab pegol, ciclosporin, daclizumab, eculizumab, efalizumab, eritoran, etanercept, everolimus, fingolimod, gliotoxin, gusperimus, infliximab, laquinimod, leflunomide, lenalidomide, mapracorat, mepolizumab, methotrexate, mizoribine, muromonab-CD3, mycophenolate mofetil, mycophenolic acid, natalizumab, neurovax, pegsunercept, pimecrolimus, pomalidomide, ridaforolimus, rilonacept, secukinumab, sirolimus, tacrolimus, teriflunomide, thalidomide, tocilizumab, umirolimus, ustekinumab, voclosporin, zotarolimus or combinations thereof.

In certain embodiments, the administration of 6-amionhexanoic acid is in combination with chlorambucil or cyclophosphamide, and optionally a corticosteroid such as prednisone or prednisolone.

In certain embodiments, the administration of 6-amionhexanoic acid is in combination with imatinib.

In certain embodiments, the administration of 6-amionhexanoic acid is in combination with cladribine.

In certain embodiments, the administration of 6-amionhexanoic acid is in combination with pentostatin.

In certain embodiments, the administration of 6-amionhexanoic acid is in combination with rituximab or interferon-alpha. In certain embodiments, the administration of 6-amionhexanoic acid is in combination with rituximab, cyclophosphamide, hydroxydaunorubicin, vincristine and optionally prednisone or prednisolone.

In certain embodiments, the administration of 6-amionhexanoic acid is in combination with cyclophosphamide, vincristine and optionally prednisone or prednisolone.

In certain embodiments, the administration of 6-amionhexanoic acid is in combination with cyclophosphamide, hydroxydaunorubicin, vincristine and optionally prednisone or prednisolone and optionally bendamustine.

In certain embodiments, in any of the above combinations, 6-amionhexanoic acid may be administered at any of the doses and regularity as provided herein.

EXPERIMENTAL

Example 1

Patients with Hematological Malignancies

Patients with chronic transfusion dependent thrombocytopenia who received prophylactic EACA in the outpatient setting were identified through a computerized database search. After initiation of EACA, prophylactic threshold-driven platelet transfusion was discontinued and patients received only therapeutic platelet transfusion in case of bleeding, except when admitted to the inpatient ward. In the inpatient ward, prophylactic platelets were routinely infused when platelets were $<10\times10^9$/L. The number of platelets transfused in the hospital in the absence of bleeding was censored. Patient demographics, diagnosis, treatment, platelet counts, duration of thrombocytopenia, transfusion history, bleeding and outcomes were captured onto study-specific case report forms. Bleeding was captured regardless of patient's location (out-patient or wards) and retrospectively scored based on the ITP WHO classification: grade 1=petechial bleed, grade 2=clinically mild blood loss, grade 3=gross blood loss requiring transfusion, and grade 4=retinal, cerebral, or debilitating blood loss. Statistics were descriptive. Characteristics of the patients are summarized in FIG. 1

Ninety-six percent had a hematological malignancy and 2 had a non-malignant hematological disorder (chronic immune thrombocytopenia, aplastic anemia). Median age was 61 (range, 17-82). Median platelet count at the time of initiation of EACA was $8\times10^9$/L (range, 1-19). Prior to initiation of EACA, median duration of thrombocytopenia was 273 days (range, 20-1463) and patients were transfused 2-3 times a week, in the outpatient setting, when platelet count were $<20\times10^9$/L. Thirty patients (68%) had a median of 4 (range, 1-12) hospitalizations of a median of 12 days duration (range, 4-23) during the course of treatment with EACA mainly for chemotherapy, but also for the management of neutropenic fever. Seventy one percent had relapsed/refractory disease; while 29% had a stable disease or were actively receiving chemotherapy at the time of EACA was administered. Ten (23%) were refractory to platelet transfusions and had platelet counts continuously $<10\times10^9$/L.

EACA was prescribed at the oral dose of 1 gram twice daily until sustained untransfused platelet count was $>30\times 10^9$/L. Median duration of administration of EACA was 47 days (range, 7-209). Patients were monitored in the outpatient clinic, with a CBC obtained at least once a week. While on EACA, 7/44(16%) patients received a median of 4 (range, 1-8) platelets transfusions to treat 10 bleeding episodes. Median score for these 10 bleeding episodes was 2 (2-4), with 1 patient experiencing a traumatic intracranial hemorrhage secondary to motor vehicle accident (grade 4), and 1 patient suffering an episode of grade 3 hematochezia from a pre-existing rectal ulcer. The other 5 patients had 8 grade 2 mucocutaneous bleeds: hemorrhoid, epistaxis, oral, bladder and vaginal. Eleven patients (25%) had 19 episodes of minor mucocutaneous (epistaxis, bruises, oral, and vaginal) that resolved spontaneously and did not require platelet transfusions. Median bleeding score for these 19 bleeding events was 1 (1-2). Of interest, only 4 of the 10 platelet refractory patients had bleeding episodes that were mucocutaneous (3 grade 1, 5 grade 2 and 1 grade 3 bleeding).

EACA was overall well tolerated and no patients discontinued EACA due to intolerance. One patient discontinued EACA due to the onset of hematuria (2%), 18 (41%) due to platelet recovery, 25 (57%) due to referral to hospice or death. No patient experienced a venous thromboembolic event.

The invention claimed is:

1. A method of reducing the likelihood of spontaneous mucocutaneous bleeding consisting of administering twice daily a pharmaceutical composition comprising about 0.5 to 2.0 grams of 6-aminohexanoic acid or molar equivalent salt or prodrug thereof to a subject wherein the subject is absent bleeding and has a measured platelet count of less than $20 \times 10^9$/L, and wherein the administration is sustained for more than 30 days or until a measured platelet count is greater than $30 \times 10^9$/L.

2. The method of claim 1, wherein the subject receives about 2.0 grams of 6-aminohexanoic acid or molar equivalent salt thereof daily.

3. The method of claim 1, wherein administration is twice daily a pharmaceutical composition comprising about 1.0 grams of 6-aminohexanoic acid or molar equivalent salt thereof.

4. The method of claim 1, wherein the subject is diagnosed with a hematological disorder.

5. The method of claim 4, wherein the hematological disorder is a hematological malignancy selected from leukemia, acute lymphoblastic leukemia (ALL), acute myelogenous leukemia (AML), chronic lymphocytic leukemia (CLL), small lymphocytic lymphoma (SLL), chronic myelogenous leukemia (CIVIL), acute monocytic leukemia (AMoL), lymphoma, Hodgkin's lymphoma, or Non-Hodgkin's lymphoma.

6. The method of claim 1, wherein the subject received an autologous or allogeneic hematopoietic stem cell transplantation, bone marrow transplant or peripheral stem cell transplantation.

7. The method of claim 1, wherein the bleeding is epistaxis of bleeding from the nose.

8. The method of claim 1, wherein the bleeding is bleeding from mouth or gums.

9. The method of claim 1, wherein the bleeding is bleeding from the bladder.

10. The method of claim 1, wherein the bleeding is bleeding of from the vagina.

11. The method of claim 1, wherein the bleeding is bleeding of from the rectum.

* * * * *